United States Patent
Maxon et al.

(10) Patent No.: US 6,861,061 B2
(45) Date of Patent: Mar. 1, 2005

(54) STABILIZATION OF VITAMINS IN WATER-IN SILICONE OIL (W/O) EMULSIONS

(75) Inventors: Bartley Dean Maxon, St. Louis, MI (US); Michael Stephen Starch, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 72 days.

(21) Appl. No.: 10/024,983

(22) Filed: Dec. 19, 2001

(65) Prior Publication Data

US 2003/0119779 A1 Jun. 26, 2003

(51) Int. Cl.[7] .................. A61K 31/525; A61K 31/51; A61K 9/00; A61K 6/00
(52) U.S. Cl. .................. 424/400; 424/401; 514/458; 514/725; 514/251; 514/276; 524/862
(58) Field of Search ................ 514/458, 725, 514/251, 276; 524/862; 424/400, 401

(56) References Cited

U.S. PATENT DOCUMENTS

| | | | |
|---|---|---|---|
| 4,150,048 A | * | 4/1979 | Schilling, Jr. et al. |
| 4,742,142 A | | 5/1988 | Shimizu et al. ............ 528/15 |
| 4,853,474 A | | 8/1989 | Bahr et al. ............ 556/445 |
| 4,980,167 A | | 12/1990 | Harashima et al. ......... 424/401 |
| 5,136,068 A | | 8/1992 | Bahr et al. ............ 556/445 |
| 5,266,321 A | | 11/1993 | Shukuzaki et al. ......... 424/401 |
| 5,599,533 A | | 2/1997 | Stepniewski et al. ..... 424/78.02 |
| 5,654,362 A | | 8/1997 | Schulz, Jr. et al. ......... 524/862 |
| 5,853,741 A | | 12/1998 | Znaiden et al. ........... 424/401 |
| 5,889,108 A | * | 3/1999 | Zhang |
| 6,168,782 B1 | | 1/2001 | Lin et al. ............. 424/78.03 |
| 6,207,717 B1 | | 3/2001 | Lin et al. ............. 514/772.1 |

FOREIGN PATENT DOCUMENTS

| | | | |
|---|---|---|---|
| EP | 0869142 | 10/1998 | ......... C08G/77/50 |
| EP | 1020175 | 7/2000 | ......... A61K/7/00 |
| EP | 1062942 | 12/2000 | ......... A61K/7/32 |
| EP | 1097968 | 5/2001 | ......... C08L/83/12 |
| WO | WO 00/72817 A1 | 12/2000 | ......... A61K/7/48 |

OTHER PUBLICATIONS

Remington's Pharmaceutical Sciences, 18th ed., 1990, p. 1314.*

* cited by examiner

*Primary Examiner*—San-Ming Hui
(74) *Attorney, Agent, or Firm*—Alan Zombeck

(57) ABSTRACT

A water-in-oil (W/O) emulsion with a discontinuous aqueous phase dispersed in a continuous oil phase has in the continuous oil phase a linear silicone polyether, an α,ω-diene crosslinked silicone elastomer, and a nonionic organic emulsifier. The W/O emulsion is otherwise free of silicone elastomers prepared using unsaturated compounds containing silicon atoms. Either the discontinuous aqueous phase of the W/O emulsion or the continuous oil phase of the W/O emulsion contains a water soluble or oil soluble active ingredient such as a vitamin.

6 Claims, No Drawings

US 6,861,061 B2

STABILIZATION OF VITAMINS IN WATER-IN SILICONE OIL (W/O) EMULSIONS

FIELD OF THE INVENTION

This invention is related to compositions and methods of incorporating and stabilizing vitamins such as Vitamin E into water-in-silicone oil emulsions (W/O). In particular, the invention involves the use of a generally linear silicone polyether as the silicone emulsifier, in combination with an organic emulsifier, to stabilize vitamins in the W/O emulsion.

BACKGROUND OF THE INVENTION

Vitamin A and Vitamin C, when incorporated into water-in-silicone oil (W/O) compositions for skin care applications, are known and have met with some degree of success in the market place.

However, the active forms of Vitamin E, i.e., tocopherol, typically have exhibited signs of degradation and instability in such W/O systems. There is, therefore, a need in the personal care arena, for stabilized vitamin, especially stabilized Vitamin E containing water-in-silicone oil emulsions (W/O).

While International Publication WO 00/72817 A1 (Dec. 7, 2000) describes certain W/O emulsions containing vitamins, the silicone elastomer component used in preparing W/O emulsions is a composition obtained by using a crosslinking agent which is an unsaturated compound containing a silicon atom, i.e., a vinyl terminated silicone.

According to the present invention, however, it was unexpectedly discovered that new and improved W/O emulsions could be obtained where such silicone elastomer compositions were omitted, and in their place was substituted a silicone elastomer composition obtained by using a crosslinking agent which is an unsaturated compound containing no silicon atoms, i.e., α,ω-diene crosslinked silicone elastomer.

BRIEF SUMMARY OF THE INVENTION

The invention is directed to compositions such as water-in-oil (W/O) emulsions having a discontinuous aqueous phase dispersed in a continuous oil phase. The continuous oil phase of the W/O emulsion contains a linear silicone polyether, an α,ω-diene crosslinked silicone elastomer, and a nonionic organic emulsifier. The W/O emulsion is free of silicone elastomers prepared using unsaturated compounds containing silicon atoms.

Preferably, either the discontinuous aqueous phase of the W/O emulsion or the continuous oil phase of the W/O emulsion contains a water soluble active ingredient or an oil soluble active ingredient, respectively.

The continuous oil phase of the W/O emulsion may include one or more solvents such as octamethylcyclotetrasiloxane, decamethylcyclopentasiloxane, dodecamethylcyclohexasiloxane, hexamethyldisiloxane, octamethyltrisiloxane, decamethyltetrasiloxane, dodecamethylpentasiloxane, tetradecamethylhexasiloxane, and hexadecamethylheptasiloxane.

These and other features of the invention will become apparent from a consideration of the detailed description.

DETAILED DESCRIPTION OF THE INVENTION

The Linear, i.e., Non-crosslinked, Silicone Polyether

The linear, i.e., non-crosslinked, silicone polyether, used to prepare compositions according to the invention, is generally dispersible in the oil phase. It can have a rake type structure wherein the polyoxyethylene or polyoxyethylene-polyoxypropylene copolymeric units are grafted onto the siloxane backbone, or the SPE can have an ABA block copolymeric structure wherein A represents the polyether portion and B the siloxane portion of an ABA structure.

Non-crosslinked silicone polyethers suitable for use herein have the formula $MD_{0-1,000}D'_{1-100}M$, most preferably the formula $MD_{0-500}D'_{1-50}M$, where M represents monofunctional unit $R_3SiO_{1/2}$, D represents difunctional unit $R_2SiO_{2/2}$, and D' represents difunctional unit $RR'SiO_{2/2}$. In these formulas, R is an alkyl group containing 1–6 carbon atoms or an aryl group, and R' is an oxyalkylene containing moiety. The R' groups may contain only oxyethylene (EO) units; a combination of oxyethylene (EO) and oxypropylene (PO) units; or a combination of oxyethylene (EO) units, oxypropylene (PO) units, and oxybutylene (BO) units. Preferred R' groups include oxyalkylene units in the approximate ratio of $EO_{3-100}PO_{0-100}$, most preferably in the ratio $EO_{3-30}PO_{1-30}$.

R' moieties typically includes a divalent radical such as —$C_mH_{2m}$— where m is 2–8 for connecting the oxyalkylene portion of R' to the siloxane backbone. Such moieties also contain a terminating radical for the oxyalkylene portion of R' such as hydrogen, hydroxyl, or an alkyl, aryl, alkoxy, or acetoxy group.

Non-crosslinked silicone polyethers useful herein can also be of a type having the formula $M'D_{10-1,000}D'_{0-100}M'$, most preferably the formula $M'D_{10-500}D'_{0-50}M'$, wherein M' represents monofunctional unit $R_2R'SiO_{1/2}$, D represents difunctional unit $R_2SiO_{2/2}$, and D' represents difunctional unit $RR'SiO_{2/2}$. In these formulas, R can be an alkyl group containing 1–6 carbon atoms or an aryl group, and again R' represents an oxyalkylene containing moiety. As noted previously, R' groups typically contain only oxyethylene (EO) units or combinations of oxyethylene (EO) and oxypropylene (PO) units. Such R' groups include these oxyalkylene units in the ratio $EO_{3-100}PO_{0-100}$, most preferably $EO_{3-30}PO_{1-30}$.

As also noted previously, R' moieties typically include a divalent radical —$C_mH_{2m}$— where m is 2–8 for connecting the oxyalkylene portions of R' to the siloxane backbone. In addition, the moiety R' contains a terminating radical for oxyalkylene portions of R' such as hydrogen, hydroxyl, an alkyl, aryl, alkoxy, or acetoxy group.

In addition, non-crosslinked silicone polyethers useful herein can having the formula $MD_{0-1,000}D'_{0-100}D''_{1-1,00}M$ wherein D" represents difunctional unit $RR''SiO_{2/2}$, and R" is an alkyl group containing 1–40 carbon atoms. M, D, D', and R, are the same as defined above.

Table 1 shows some representative linear, i.e., non-crosslinked, silicone polyethers conforming to these formulas which can be used in preparing emulsions according to the invention.

TABLE 1

| Linear Silicone Polyether | Nominal Structure of Linear, i.e., Non-Crosslinked, Silicone Polyether |
|---|---|
| A | $MD_{8.6}D'_{3.6}M$ where R is —$CH_3$ and R' is —$(CH_2)_3(EO)_{12}OH$ |
| B | $MD_{108}D'_{10}M$ where R is —$CH_3$ and R' is —$(CH_2)_3(EO)_{10}(PO)_4OH$ |

TABLE 1-continued

| Linear Silicone Polyether | Nominal Structure of Linear, i.e., Non-Crosslinked, Silicone Polyether |
|---|---|
| C | M'D'$_{75}$M' where R is —CH$_3$ and R' is —(CH$_2$)$_3$(EO)$_{18}$(PO)$_{18}$OAc |
| D | M'D'$_{50}$M' where R is —CH$_3$ and R' is —(CH$_2$)$_3$(EO)$_{18}$(PO)$_{18}$OH |
| E | M'D'$_{13}$M' where R is —CH$_3$ and R' is —(CH$_2$)$_3$(EO)$_{12}$OH |
| P | MD$_{22}$D'$_2$M where R is —CH$_3$ and R' is —(CH$_2$)$_3$(EO)$_{12}$(PO)$_{12}$OH |
| G | MD$_{396}$D'$_4$M where R is —CH$_3$ and R' is —(CH$_2$)$_3$(EO)$_{18}$(PO)$_{18}$OH |

The Volatile Silicone, i.e., The Solvent

The solvent used herein is a volatile silicone, generally a low molecular weight silicone oil, and most typically a cyclic alkyl siloxane of the formula (R'''$_2$SiO)$_d$ or a linear alkyl siloxane of the formula R'''$_3$SiO(R'''$_2$SiO)$_e$SiR'''$_3$ in which R''' is an alkyl group containing 1–6 carbon atoms, d is 3–6 and e is 0–5. Most preferred, however, are volatile cyclic methyl siloxanes of the formula {(CH$_3$)$_2$SiO}$_d$ and volatile linear methyl siloxanes of the formula (CH$_3$)$_3$SiO{(CH$_3$)$_2$SiO}$_e$Si(CH$_3$)$_3$ and in which d is 3–6 and e is 0–5, respectively. Preferably, the volatile methyl siloxane has a boiling point less than 250° C. and a viscosity of 0.65–5.0 centistoke (mm$^2$/s).

Some representative linear volatile methyl siloxanes are hexamethyldisiloxane (MM) with a boiling point of 100° C., viscosity of 0.65 mm$^2$/s, and formula Me$_3$SiOSiMe$_3$; octamethyltrisiloxane (MDM) with a boiling point of 152° C., viscosity of 1.04 mm$^2$/s, and formula Me$_3$SiOMe$_2$SiOSiMe$_3$; decamethyltetrasiloxane (MD$_2$M) with a boiling point of 194° C., viscosity of 1.53 mm$^2$/s, and formula Me$_3$SiO(Me$_2$SiO)$_2$SiMe$_3$; dodecamethylpentasiloxane (MD$_3$M) with a boiling point of 229° C., viscosity of 2.06 mm$^2$/s, and formula Me$_3$SiO(Me$_2$SiO)$_3$SiMe$_3$; tetradecamethylhexasiloxane (MD$_4$M) with a boiling point of 245° C., viscosity of 2.63 mm$^2$/s, and formula Me$_3$SiO(Me$_2$SiO)$_4$SiMe$_3$; and hexadecamethylheptasiloxane (MD$_5$M) with a boiling point of 270° C., viscosity of 3.24 mm$^2$/s, and formula Me$_3$SiO(Me$_2$SiO)$_5$SiMe$_3$. Me in these and the following formulas represents the methyl group CH$_3$.

Some representative cyclic volatile methyl siloxanes are hexamethylcyclotrisiloxane (D$_3$), a solid at room temperature, with a boiling point of 134° C. and formula (Me$_2$SiO)$_3$; octamethylcyclotetrasiloxane (D$_4$) with a boiling point of 176° C., viscosity of 2.3 mm$^2$/s, and formula (Me$_2$SiO)$_4$; decamethylcyclopentasiloxane (D$_5$) with a boiling point of 210° C., viscosity of 3.87 mm$^2$/s, and formula (Me$_2$SiO)$_5$; and dodecamethylcyclohexasiloxane (D$_6$) with a boiling point of 245° C., viscosity of 6.62 mm$^2$/s, and formula (Me$_2$SiO)$_6$.

The Silicone Gum

The silicone gum is a high molecular weight, most typically a silanol functional polymer, but including polydimethylsiloxane gums as well. Such gums are known in the art and are readily available commercially from vendors such as the Dow Corning Corporation, Midland, Mich. Such materials have a structure generally corresponding to the formula:

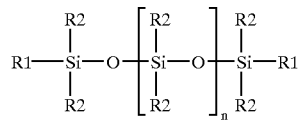

in which n is an integer of 5,000–50,000, preferably 10,000–50,000. R1 represents —OH; an alkyl group having 1–6 carbon atoms such as methyl, ethyl, or propyl; an aryl group such as phenyl or xenyl; an alkaryl group such as tolyl or xylyl; or an aralkyl group such as benzyl, phenylethyl, or 2-phenylpropyl. R2 represents an alkyl group having 1–6 carbon atoms such as methyl, ethyl, or propyl; an aryl group such as phenyl or xenyl; an alkaryl group such as tolyl or xylyl; or an aralkyl group such as benzyl, phenylethyl, or 2-phenylpropyl. Silicone gums in which R1 is an alkenyl group such as vinyl can also be employed. Most preferred, however, are silicone gums in which R1 is —OH and R2 is methyl; and silicone gums in which both R1 and R2 are methyl.

α,ω-Diene Crosslinked Silicone Elastomer

As used herein, the term α,ω-diene crosslinked silicone elastomer is intended to mean α,ω-diene crosslinked silicone elastomers having no oxyalkylene units in their structure. They have been referred to generally in the art as non-emulsifying silicone elastomers, meaning that polyoxyalkylene units are absent. Otherwise, the α,ω-diene crosslinked silicone elastomers suitable for use according to this invention are the compositions described in U.S. Pat. No. 5,654,362 (Aug. 5, 1997).

As described in detail in the '362 patent, the α,ω-diene crosslinked silicone elastomers are prepared by reacting (A) an ≡Si—H containing polysiloxane of the formula R$_3$SiO (R'$_2$SiO)$_a$(R''HSiO)$_b$SiR$_3$ and optionally an ≡Si—H containing polysiloxane of formula HR$_2$SiO(R'$_2$SiO)$_c$SiR$_2$H or formula HR$_2$SiO(R'$_2$SiO)$_a$(R''HSiO)$_b$SiR$_2$H where R, R', and R'' are alkyl groups with 1–6 carbon atoms; a is 0–250; b is 1–250; and c is 0–250; with (B) an alpha, omega-diene of formula CH$_2$=CH(CH$_2$)$_x$CH=CH$_2$ where x is 1–20. The reaction is conducted in the presence of a platinum catalyst and in the presence of (C) a low molecular weight silicone oil or other solvent. The reaction system is non-aqueous in contrast to the reaction system used to prepare silicone rubber powders.

Silicone Rubber Powder

As used herein, the term silicone rubber powder is intended to mean compositions prepared generally according to methods described in U.S. Pat. No. 4,742,142 (May 3, 1988).

Silicone rubber powders, sometimes referred to as E-Powders, are spherical particles of vulcanized silicone rubber, i.e., crosslinked polydimethylsiloxanes (PDMS), having a mean particle size distribution on the order of 0.1–200 μm. An aqueous emulsion process is used to prepare the silicone rubber powder as this process leads to a spherical shape for the particles, and it provides the desirable particle size distribution. In essence, the emulsion process consists of emulsifying a curable, liquid silicone elastomeric composition in water with one or more surface active agents followed by a curing step and finally removal of water. Inherent to the emulsion process are the spherical shape of the particles and a relatively good control of particle size distribution within a certain region.

Two curing reactions for crosslinking siloxane polymers are generally utilized, one being addition of a silicon hydride (≡SiH) to a vinyl functional siloxane in the presence of a platinum catalyst, i.e., hydrosilylation, and the other condensation of silanol functional siloxanes with reactive silicon. Polymers used to make silicone rubber powder are either OH or vinyl functional polymers, depending upon whether condensation or hydrosilylation is used for the crosslinking step. These polymers are usually of moderately low molecular weight (MW), such that their concomitant low viscosity make them easy to emulsify by conventional techniques. Polymers having viscosities under about 1000 cP (centipoise) are preferred for preparing silicone rubber powder.

Crosslinking agents can be practically any multifunctional reactive siloxane or silane that is soluble in the polymer. Silicon hydride ($\equiv$SiH) functional siloxanes are the crosslinkers of choice due to their high reactivity and the absence of byproducts. These can be either linear polymethylhydrogen siloxane or copolymers of polydimethylsiloxane polymethylhydrogen siloxane. The hydrosilylation reaction involving addition of $\equiv$SiH to a vinyl functional siloxane has the advantage that no byproducts are formed. In contrast, copious amounts of $H_2$ are liberated from the condensation route involving reaction of $\equiv$SiH with $\equiv$SiOH.

The emulsification procedure is carried out using standard emulsion high shear equipment such as homogenizers or colloid mills. Surface active agents used can be either ionic or nonionic, or a combination of both, but nonionic is preferred. Preferred nonionic surfactants are alkyl ethoxylates. Levels of surfactant is on order of 0.5–5 percent by weight of the silicone polymer. It should be understood that the surface active agents remain with the silicone rubber powder upon removal of water.

Crosslinking in silicone rubber powders must occur after the particles have been formed. However, crosslinking will commence upon combining the three basic ingredients, (i) the functional polymer, (ii) the crosslinking agent, and (iii) the catalyst. Thus, some means must be used to ensure particle formation is complete prior to the onset of significant crosslinking. This can be accomplished by using catalyst inhibitors or by adding the catalyst after emulsification. In some cases, the emulsion is heated to increase the rate of crosslinking reactions. Once crosslinking is complete, the particles are harvested by removing water. Water removal can be accomplished by using processes like vacuum distillation or spray drying. In vacuum distillation, a mixer is used to provide heat and agitation under vacuum. Spray drying is the preferred method, however, as it is highly efficient and can be operated continuously.

The Partially Crosslinked Silicone Polyether

The secondary silicon based emulsifier used in the examples in this application is a silicone composition generally as described in detail in U.S. Pat. Nos. 4,853,474 (Aug. 1, 1989) and 5,136,068 (Aug. 4, 1992), each of which teach methods of making such partially crosslinked compositions. These compositions are also readily available on a commercial basis from vendors such as the Dow Corning Corporation, Midland, Mich.

The Organic Emulsifier(s)

As used herein, the term organic emulsifiers is intended to exclude emulsifiers containing silicon atoms. The organic emulsifier is otherwise a nonionic surfactant. Some suitable types of nonionic surfactants are carboxylated alcohol ethoxylates, carboxylated alkylphenol ethoxylates, ethoxylated alcohols, ethoxylated fatty acids, ethoxylated fatty esters, ethoxylated fatty oils, glycerol esters, polyglycerol fatty esters, ethoxylated glycerol esters, sorbitan derivatives, sucrose esters and derivatives, and glucose esters and derivatives. Examples of organic emulsifiers most representative of the invention are ethoxylated fatty esters such as EMULSYNT 1055 and sorbitan derivatives such as TWEEN 20. EMULSYNT 1055 in particular is a mixture of a polyglycerol fatty ester and an ethoxylated fatty ester, namely polyglycerol-4 oleate and PEG-8 propylene glycol cocoate. TWEEN 20 on the other hand is polyoxyethylene (20) sorbitan monolaurate.

The Active Ingredient

Water soluble vitamins and water soluble drugs are some examples of representative active ingredients which can be incorporated into compositions according to the invention, among which are Vitamin $B_1$, Vitamin $B_2$, Vitamin $B_6$, Vitamin $B_{12}$, niacin, folic acid, biotin, and pantothenic acid.

In addition, the compositions may also contain oil soluble active ingredients such as vitamins and drugs, among which are Vitamin E, Tocopherol, esters of Vitamin E, α-Tocopherol, β-Tocopherol, γ-Tocopherol, Δ-Tocopherol, Tocophersolan, Tocopheryl Acetate, Tocopheryl Palmitate, Tocopheryl Linoleate, Tocopheryl Nicotinate, Tocopheryl Succinate, and mixtures thereof.

Salt Component

As used herein, the term "salt" is intended to mean an inorganic salt or an organic salt, including compounds commonly referred to as electrolytes.

Some examples of suitable inorganic salts include calcium chloride, magnesium sulfate, magnesium chloride, sodium sulfate, sodium thiosulfate, sodium chloride, sodium phosphate, ammonium chloride, ammonium carbonate, iron sulfate, aluminum sulfate, aluminum chloride, aluminum chlorohydrate, aluminum sesquichlorohydrate, aluminum dichlorohydrate, aluminum zirconium tetrachorohydrex glycine, aluminum zirconium trichlorohydrate, aluminum zirconium tetrachlorohydrate, aluminum zirconium pentachlorohydrate, and aluminum zirconium octachlorohydrate.

Some examples of suitable organic salts include sodium aluminum lactate, sodium acetate, sodium dehydroacetate, sodium butoxy ethoxy acetate, sodium caprylate, sodium citrate, sodium lactate, sodium dihydroxy glycinate, sodium gluconate, sodium glutamate, sodium hydroxymethane sulfonate, sodium oxalate, sodium phenate, sodium propionate, sodium saccharin, sodium salicylate, sodium sarcosinate, sodium toluene sulfonate, magnesium aspartate, calcium propionate, calcium saccharin, calcium d-saccharate, calcium thioglycolate, aluminum caprylate, aluminum citrate, aluminum diacetate, aluminum glycinate, aluminum lactate, aluminum methionate, aluminum phenosulfonate, potassium aspartate, potassium biphthalate, potassium bitartrate, potassium glycosulfate, potassium sorbate, potassium thioglycolate, potassium toluene sulfonate, and magnesium lactate.

Optional Components

Since emulsions are susceptible to microbiological contamination, a preservative may be required as an optional component of the composition, and some representative compounds which can be used include formaldehyde, salicylic acid, phenoxyethanol, DMDM hydantoin (1,3-dimethylol-5,5-dimethyl hydantoin), 5-bromo-5-nitro-1,3-dioxane, methyl paraben, propyl paraben, sorbic acid, imidazolidinyl urea sold under the name GERMALL® II by Sutton Laboratories, Chatham, N.J., sodium benzoate, 5-chloro-2-methyl-4-isothiazolin-3-one sold under the name KATHON CG by Rohm & Haas Company, Philadelphia, Pa., and iodopropynl butyl carbamate sold under the name GLYCACIL® L by Lonza Incorporated, Fair Lawn, N.J.

A freeze/thaw stabilizer can be included as an optional component of the composition including compounds such as ethylene glycol, propylene glycol, glycerol, and trimethylene glycol.

Another optional component of the emulsion which can be included is a corrosion inhibitor such as an alkanolamine, an inorganic phosphate such as zinc dithiophosphate, an inorganic phosphonate, an inorganic nitrite such as sodium nitrite, a silicate, a siliconate, an alkyl phosphate amine, a succinic anhydride such as dodecenyl succinic anhydride, an amine succinate, or an alkaline earth sulfonate such as sodium sulfonate or calcium sulfonate.

Chelating agents such as ethylene diamine tetraacetic acid (EDTA) and nitrilotriacetic acid (NTA) can also be included.

Compositions according to the present invention can be formed by combining the various components of the oil phase A and the water phase B in the following representative amounts, expressed in ranges as weight percent.

(i) 0.2–3.0 percent of the silicone emulsifier(s) based on 100 percent of the emulsifier, not including any solvent;
(ii) 20–80 percent of the volatile silicone;
(iii) 0–8 percent of the silicone gum based on 100 percent of the gum, not including any solvent;
(iv) 0.2–10 percent of the silicone elastomer based on 100 percent of the elastomer, not including any solvent;
(v) 0–5 percent of the silicone rubber powder for compositions not according to this invention;
(vi) 0.1–4 percent of the organic emulsifier(s) including emulsifiers used in the oil phase and in the water phase;
(vii) 15–75 percent of water;
(viii) 0.1–3 percent of the electrolyte, i.e., sodium chloride;
(ix) 0.1–3 percent of the chelating agent, i.e., EDTA, or other optional component; and
(x) 0.1–8 percent of the active ingredient(s), i.e., vitamins.

The compositions according to the invention can be prepared mechanically, and this simply involves mixing the oil phase and the water phase together and homogenizing the phase mixture using a laboratory homogenizer or other device for applying vigorous agitation.

EXAMPLES

The following examples are set forth in order to illustrate the invention in more detail.

Examples I–III

As shown in Table 2, three Vitamin E W/O compositions were prepared. The ingredients used to make the compositions are shown in amounts expressed in percent by weight. Comparative Examples I and II showed almost immediate signs of separation, or exhibited color changes within about two days; whereas W/O compositions as in Example III which is according to the invention, were stable for periods of time ranging from about seven weeks when stored at 50° C., and for as long as five months when stored at room temperature.

TABLE 2

| Phase A | Description - Oil Phase | I - Comparative | II- Comparative | III - Invention |
|---|---|---|---|---|
| Primary Silicone Emulsifier | 10% of Linear, i.e., Non-Crosslinked, Silicone Polyether & 90% of $D_5$ | 8.5 | 10.0 | 8.5 |
| Volatile Silicone | Decamethylcyclopentasiloxane ($D_5$) | 16.25 | 20.0 | 18.0 |
| Silicone Gum & Volatile Silicone | 15% of OH Endblocked Polysiloxane & 85% of $D_5$ | 1.0 | 1.0 | 2.0 |

TABLE 2-continued

| | | | | |
|---|---|---|---|---|
| Silicone Elastomer | 12% of α,ω-Diene Crosslinked Silicone Elastomer & 88% of $D_5$ | 3.0 | 5.0 | 3.0 |
| Silicone Powder | Silicone Rubber Powder | 2.5 | 0.5 | None |
| Primary Organic Emulsifier | Nonionic Surfactant, Emulsynt 1055, Polyglycerol-4 Oleate & PEG-8 Propylene Glycol Cocoate | None | None | 2.0 |
| Secondary Silicone Emulsifier | Partially Crosslinked Silicone Polyether | None | 1.0 | None |

| Phase B | Description - Water Phase | I - Comparative | II - Comparative | III - Inventive |
|---|---|---|---|---|
| $H_2O$ | Water | 66.5 | 60.7 | 64.7 |
| Secondary Organic Emulsifier | Polyoxyethylene (20) Sorbitan Monolaurate - TWEEN 20 | 0.5 | 0.5 | 0.5 |
| Electrolyte | Sodium Chloride | 1.0 | 1.0 | 1.0 |
| Chelating Agent | Ethylenediamine Tetraacetic Acid, EDTA | 0.1 | 0.1 | 0.1 |
| Vitamin E | Tocopherol | 0.7 | 0.7 | 0.7 |

In Comparative Example I, it was observed that the viscosity dropped when tocopherol was added, and there was an almost immediate separation. In Comparative Example II, only a slight drop in viscosity was observed. The silicone rubber powder used in Comparative Example II, it is noted, was post added. However, the W/O composition in Comparative Example II remained stable for only a few days. In Example III, which is according to the present invention, the viscosity of the W/O composition remained stable throughout the whole process of preparing the composition. The W/O composition remained stable for five months storage at room temperature in a plastic container.

100 gram portions were used in preparing the three W/O compositions shown in Table 2. These W/O compositions were prepared by combining the silicone emulsifiers, the volatile silicone, the silicone gum, the silicone elastomer; and/or the silicone rubber powder, the primary organic emulsifier, used in forming the oil Phase A for some of the compositions. The components used for forming aqueous Phase B were dispersed in a separate container. Aqueous Phase B was slowly added to oil phase B and mixed under turbulent conditions. The time of addition of Phase B to oil Phase A was about 15–20 minutes. Combined Phases A and B were then mixed together for an additional period of 15–20 minutes to form the final W/O compositions.

It should be noted that Comparative Examples I and II each show W/O emulsions in which the silicone component, i.e., the Silicone Rubber Powder, was a composition obtained by using a crosslinking agent which is an unsaturated compound containing a silicon atom, i.e., a vinyl terminated silicone. In contrast, Example III, which is the example according to the present invention, omits the Silicone Rubber Powder, and in its place uses an α,ω-diene crosslinked silicone elastomer.

Compositions prepared according to the invention can be used in various over-the-counter (OTC) personal care products. Thus, they can be used in antiperspirants, deodorants, skin creams, skin care lotions, moisturizers, facial treatments such as acne or wrinkle removers, personal and facial cleansers, bath oils, perfumes, colognes, sachets, sunscreens, pre-shave and after-shave lotions, liquid soaps, shaving soaps, shaving lathers, hair shampoos, hair conditioners, hair sprays, mousses, permanents, depilatories, cuticle coats, make-ups, color cosmetics, foundations, blushes, lipsticks, lip balms, eyeliners, mascaras, oil removers, color cosmetic removers, and powders. The compositions are also useful as carriers for pharmaceuticals, biocides, herbicides, pesticides, and to incorporate various types of water soluble substances and oil soluble substances into hydrophilic and hydrophobic systems.

Other variations may be made in compounds, compositions, and methods described herein without departing from the essential features of the invention. The embodiments of the invention specifically illustrated herein are exemplary only and not intended as limitations on their scope except as defined in the appended claims.

What is claimed is:

1. A composition comprising a water-in-oil (W/O) emulsion having a discontinuous aqueous phase dispersed in a continuous oil phase, the continuous oil phase of the W/O emulsion comprising a linear silicone polyether, the linear silicone polyether having a rake type structure wherein the polyoxyethylene or polyoxyethylene-polyoxypropylene copolymeric units are grafted onto a siloxane backbone, or the linear silicone polyether having an ABA block copolymeric structure wherein A represents the polyether portion and B represents the siloxane portion of an ABA structure; a non-emulsifying $\alpha,\omega$-diene crosslinked silicone elastomer having no oxyalkylene units in its structure; and a nonionic organic emulsifier selected from the group consisting of carboxylated alcohol ethoxylates, carboxylated alkylphenol ethoxylates, ethoxylated alcohols, ethoxylated fatty acids, ethoxylated fatty esters, ethoxylated fatty oils, glycerol esters, polyglycerol fatty esters, ethoxylated glycerol esters, sorbitan derivatives, sucrose esters and their derivatives, and glucose esters and their derivatives; the W/O emulsion being free of silicone elastomers prepared using unsaturated compounds containing silicon atoms.

2. A composition according to claim 1 in which one of the discontinuous aqueous phase of the W/O emulsion or the continuous oil phase of the W/O emulsion contains a water soluble active ingredient or an oil soluble active ingredient, respectively.

3. A composition according to claim 2 in which the active ingredient is selected form the group consisting of Vitamin $B_1$, Vitamin $B_2$, Vitamin $B_6$, Vitamin $B_{12}$, niacin, folic acid, biotin, pantothenic acid, Vitamin E, Tocopherol, $\alpha$-Tocopherol, $\beta$-Tocopherol, $\gamma$-Tocopherol, $\Delta$-Tocopherol, Tocophersolan, Tocopheryl Acetate, Tocopheryl Palmitate, Tocopheryl Linoleate, Tocopheryl Nicotinate, Tocopheryl Succinate, and mixtures thereof.

4. A composition according to claim 1 in which the continuous oil phase of the W/O emulsion contains 0.2–3.0 percent by weight of the linear silicone polyether, 0.2–10 percent by weight of the $\alpha,\omega$-diene crosslinked silicone elastomer, and 0.1–4.0 percent by weight of the nonionic organic emulsifier, the balance of the W/O emulsion containing a solvent and water.

5. A composition according to claim 4 in which the solvent is a volatile cyclic alkyl siloxane with the formula $(R'''_2SiO)_d$ or a volatile linear alkyl siloxane with the formula $R'''_3SiO(R'''_2SiO)_eSiR'''_3$ in which R''' is an alkyl group containing 1–6 carbon atoms, d is 3–6 and e is 0–5.

6. A composition according to claim 5 in which the solvent is selected from the group consisting of hexamethylcyclotrisiloxane, octamethylcyclotetrasiloxane, decamethylcyclopentasiloxane, dodecamethylcyclohexasiloxane, hexamethyldisiloxane, octamethyltrisiloxane, decamethyltetrasiloxane, dodecamethylpentasiloxane, tetradecamethylhexasiloxane, and hexadecamethylheptasiloxane.

* * * * *